United States Patent
Yuen

(10) Patent No.: US 8,897,835 B2
(45) Date of Patent: Nov. 25, 2014

(54) PERFORMANCE MONITORING MODULES AND APPARATUS

(75) Inventor: Paul Anthony Yuen, Hong Kong (CN)

(73) Assignee: Dayton Technologies Limited, New Territories (HK)

(*) Notice: Subject to any disclaimer, the term of this patent is extended or adjusted under 35 U.S.C. 154(b) by 24 days.

(21) Appl. No.: 13/499,332

(22) PCT Filed: Sep. 30, 2010

(86) PCT No.: PCT/IB2010/054418
§ 371 (c)(1),
(2), (4) Date: Jun. 14, 2012

(87) PCT Pub. No.: WO2011/039722
PCT Pub. Date: Apr. 7, 2011

(65) Prior Publication Data
US 2012/0252530 A1   Oct. 4, 2012

(30) Foreign Application Priority Data
Sep. 30, 2009   (HK) .................................. 09109094.7

(51) Int. Cl.
*H04M 1/00* (2006.01)
*G01C 22/00* (2006.01)
(Continued)

(52) U.S. Cl.
CPC ............ *G01C 22/00* (2013.01); *A63B 2220/72* (2013.01); *A63B 2244/20* (2013.01); *A63B 2220/16* (2013.01); *H04L 67/125* (2013.01); *H04M 2250/12* (2013.01); *A63B 2071/0663* (2013.01); *A63B 2220/17* (2013.01); *A63B 69/0028* (2013.01); *A63B 71/0622* (2013.01); *A63B 2230/50* (2013.01); *A61B 5/222* (2013.01); *A63B 2230/207* (2013.01); *A63B 2220/74* (2013.01); *A63B 2220/12* (2013.01); *A63B 2230/30* (2013.01); *A63B 2225/50* (2013.01); *G06F 3/011* (2013.01); *A63B 69/16* (2013.01); *A63B 2230/06* (2013.01); *H04M 1/72527* (2013.01); *A63B 2220/75* (2013.01); *A63B 2230/202* (2013.01); *A63B 24/0062* (2013.01); *A63B 2220/76* (2013.01)
USPC ........................................ 455/556.1; 455/557

(58) Field of Classification Search
CPC .................................................... A63B 24/0062
USPC .................. 455/556.1, 557, 575.1, 575.6, 455/575.8–575.9, 90.1–90.3; 482/8–9
See application file for complete search history.

(56) References Cited

U.S. PATENT DOCUMENTS 6,002,982 A * 12/1999 Fry .............................. 701/454
2002/0015060 A1   2/2002 Honjas
(Continued)

FOREIGN PATENT DOCUMENTS

KR   10-2008-0050646 A   6/2008
WO   WO 2009/090509 A2   7/2009

OTHER PUBLICATIONS

International Search Report (PCT/ISA/210) issued on Feb. 17, 2011, by Chinese Patent Office as the International Searching Authority for International Application No. PCT/IB2010/054418.

*Primary Examiner* — Christian Hannon
(74) *Attorney, Agent, or Firm* — Buchanan Ingersoll & Rooney PC

(57) ABSTRACT

A portable performance monitoring module comprising a signal receiver, a processor for generating and outputting performance data, and a communication interface for facilitating data communication with a portable telecommunications device. The performance monitoring module is arranged to communicate with the portable telecommunications device via the communication interface upon receipt of requests from the portable telecommunications device. This module is adapted for cooperative operation with a general power telecommunications device to expand its processing and display power while maintaining a low cost simple design and compactness.

21 Claims, 9 Drawing Sheets

(51) Int. Cl.
*H04L 29/08* (2006.01)
*A61B 5/22* (2006.01)
*G06F 3/01* (2006.01)
*H04M 1/725* (2006.01)
*A63B 24/00* (2006.01)
*A63B 71/06* (2006.01)
*A63B 69/00* (2006.01)
*A63B 69/16* (2006.01)

(56) References Cited

U.S. PATENT DOCUMENTS

2008/0200312 A1* 8/2008 Tagliabue .................. 482/9
2010/0112536 A1* 5/2010 Claassen et al. ........... 434/258
2010/0280792 A1 11/2010 Paiva Velhote Correia et al.

* cited by examiner

PERFORMANCE MONITORING MODULES AND APPARATUS

FIELD OF THE INVENTION

The present invention relates to performance monitoring modules and apparatus, and more particularly to portable or mobile sports performance monitoring modules and apparatus, such as bicycle computers, runner's computers, swimmer's computers and the like. More specifically, the present invention relates to bicycle computer modules and bicycle computer apparatus.

BACKGROUND OF THE INVENTION

A performance monitoring apparatus, also known as a 'sports performance monitoring apparatus', 'sports monitor' or 'sports computer' in short, is typically configured to collect performance and/or physiological data of a person while doing sports or other physical exercises, and to analyze the collected data to provide feedback information to a user. Typical feedback information usually includes performance indicators and/or physiological conditions of a user. Typically collected performance indicators include, for example, physical performance data such as running speed, acceleration, step width, and running cadence in the case of a runner's computer; cycling speed, cycling cadence, and cycling power in the case of a bicycle computer; stroke count, stroke time, stroke count per lap, swimming speed, and stroke span in the case of a swimmer's computer.

Typically collected physiological data include, for example, heart-rate, electrocardiogram ("ECG") signals, blood pressure, blood sugar, blood oxygen level of a sportsperson when performing physical exercise. The collected data may be used for analyzing the physical performance characteristics of a sportsperson to tailor make training programs, to evaluate the strength and weakness, to understand the physiological behaviors, patterns, and/or to evaluate or extrapolate the physiological and performance limits of the sportsperson.

In order to provide more comprehensive information for evaluation, extrapolation and correlation, sports monitors may also include peripheral accessories such as barometer, compass, humidity meter, tilt meter, wind meter, GPS, etc to provide environmental or geographic information.

Mobile sports monitors are usually carried by a sportsperson either on the body or on a moving object powered by the sportsperson. As such, they are compact and lightweight in order to minimize the deadweight and motion resistance. For example, a typically good bicycle computer would weigh less than 80 grams and occupies less than 30 cm$^3$, which is of about bite-size.

Due to these general constraints, a mobile sports monitor is usually equipped with only minimum or essential components necessary to perform the minimum specific functionality, and do not provide other useful or cosmetic functions. For example, a typical mobile performance monitor usually only includes a basic micro-controller with built-in memory for data logging and display. The logged data are usually overwritten when new data are logged, as the available memory space is severely limited. The micro-controller is only a simple micro-processor programmed with basic functions for power saving, and the display is typically a monochrome dot-matrix LCD display adapted primarily for simple textual display. However, such minimum functionality may not meet the requirements of the more sophisticated sportspersons or their support team such as the coach or crew members. For example, a sports monitor with a small memory could not store and log enough data for comprehensive sports performance profile analysis. Yet, a substantial increase in memory space and processing power would have a consequence of a more bulky monitor, a more powerful processor, a more powerful battery and a more expensive device.

In light of the above, it would be appreciated that traditional sports monitors are always a product of compromise which is adapted to strike a balance among costs, compactness and performance.

Furthermore, a sports computer is typically customized for operation with a designated sensor for detecting the characteristic motion of a specific sport. As such, different sports computers will have to be used for different sports and this means a sports person will have to carry several bulky and expensive sports computers if high performance sports computers are required.

Therefore, it would be advantageous if there could be provided sports monitors that would mitigate the functionality limitations of conventional apparatus while maintaining the advantages of a special purpose device, such as low cost, low-weight, easy to use and compact.

SUMMARY OF INVENTION

According to the present invention, there is provided a portable performance monitoring module comprising a signal receiver arranged to collect performance signals from at least one performance sensors; a processor adapted for processing the collected performance signals to generate performance data, and for outputting the performance data to a general purpose portable telecommunications device; and a communication interface for facilitating data communication with the portable telecommunications device; wherein the performance monitoring module or the processor of the performance monitoring module is arranged to communicate with the portable telecommunications device via the communication interface upon receipt of requests from the portable telecommunications device.

According to another aspect of the present invention, there is provided a performance monitoring apparatus comprising a performance monitoring module of the present invention and a general purpose portable telecommunications device.

In an exemplary embodiment, the performance monitoring module is a bicycle computer module adapted for cooperative operation with a general purpose portable telecommunications device.

In another exemplary embodiment, the performance monitoring apparatus is a bicycle computer apparatus including bicycle computer module in cooperation with a general purpose portable telecommunications device.

With the built-in data communication capability connected to the processor, the performance monitor module could tap into and utilize a vast pool of resources of a much more powerful general purpose portable telecommunications device, such as a netbook computer, a mobile telephone or a mobile smart phone such as i-phone® or i-pod®, or a superphone. For example, by tapping into the processing power of a general purpose portable telecommunications device, which is typically equipped with a 32- or 64-bit high speed microprocessor such as ARM's® Cortex-A8 processor commonly used in smart phones, a much more powerful and versatile portable performance monitoring apparatus is readily available to a user by utilizing a simple, compact and low-cost purpose-built monitoring module without the need to purchase an expensive, powerful but bulky designated monitoring apparatus for each specific purpose. Such a purpose-built monitoring module is advantageous because a user can select a portable monitoring module designed for a specific purpose for cooperative use a general purpose mobile telecommunications device and by activating a customized application program. As such, a single mobile telecommunications device could be readily configured into a variety of performance monitoring apparatus at minimal costs. The use of a general purpose mobile telecommunications is particularly advantageous because new versions of application programs could be readily download.

The processor may be arranged to cause transfer of the performance data to the portable telecommunications device for display or for further processing upon receipt of requests or instructions from the portable telecommunications device.

As an example, the performance monitoring module may be arranged to collect signals from a plurality of sensors, the processor may be adapted to process the collected signals using predetermined algorithms or methodology according to the source of the collected signals to generate data.

The sensors may include performance sensors, such as cadence sensor, speed sensor, power sensor, step sensor, lap count sensor, swimming stroke sensor, or the like; and non-performance sensors, such as environmental sensors including atmospheric pressure sensor, humidity sensor, temperature sensor, UV sensor, wind speed sensor, GPS module, or the like; or physiological parameter sensors, such as body temperature sensor, heart rate sensor, ECG sensor, blood sugar sensor, blood pressure sensor, blood oxygen sensor, or the like.

The processor may be arranged as a slave processor to respond to instructions of the portable telecommunications device, to transmit performance data to the portable telecommunications device, and/or to vary the type of performance data to be transmitted to the portable telecommunications device, according to the instructions of the portable telecommunications device. As a slave processor is only required to do frontend processing, a low-cost, low-speed, and low-power consumption microprocessor could be used. To minimize wired connections, the receiver may comprise a wireless receiver frontend for receiving wireless signals from the sensors.

The performance monitoring module may comprise an adapter for plug-in or press-fitted mating connection with the portable mobile telecommunications device to establish a data communication link.

The adapter may be arranged such that mating connection between the performance monitoring module and the portable telecommunications device results in electrical connection of the communication interface with the portable telecommunications device. The adapter may be arranged for axial insertion into the portable telecommunications device. The performance monitoring module and the general purpose portable telecommunications device are detachably attachable via mechanical mating connection means.

These and other connection arrangements facilitate convenient use of the performance module.

The performance monitoring module may be fitted on a rigid housing, preferably a waterproof housing, and more preferably a housing having a bite-size volume of less than 30 cm$^3$. With a module of such a small size, a user could readily carry a number of different purpose-built performance modules for use without significant increase in dead-load.

The performance monitoring module may further comprise a display for displaying performance data and a toggle switch, wherein the type of performance data to be instantaneously displayed is selectable by a user through toggling of the toggle switch.

When configured as a performance monitoring apparatus together with a performance monitoring module, the portable telecommunications device may be adapted to control operation of the processor of the performance monitoring module as a slave processor. As the portable telecommunications device is in control, application programs stored in the telecommunications device could be used to manipulate data collected by the performance monitoring module to produce useful information for a user.

In an embodiment, the portable telecommunications device is user activate-able to capture, log, save and/or process for display performance data collected by the performance monitoring module.

In another embodiment, the portable telecommunications device is arranged to process performance data collected by the performance monitoring module and/or data collected by the portable telecommunications device from a telecommunications network or other sources to generate information for use by a user. As a typical general purposes telecommunications device is already equipped with the 2G, 3G, 4G or even satellite communication capabilities, the performance monitoring apparatus could readily tap into a vast pool of information to obtain data which are readily and very economically available through a telecommunications network.

In a further embodiment, the data collected by the portable telecommunications device from a telecommunications network include geographical guidance data such as GPS data, road, path, slope or landscape conditions or data, map data, altitude data, distance-to-target data, amenities or like data; or weather data such as atmospheric pressure, cloud, rain, sunshine data, or like data.

To further utilize the pool of information available through a telecommunications network and tap into the vast processing power and memory space of a portable telecommunications device to produce more useful information for a user, the performance monitoring apparatus may be adapted such that the portable telecommunications device is arranged to log and save both the performance data collected by the performance monitoring module and data collected from the telecommunications network.

For example, the portable telecommunications device may be adapted to process or analyze the logged performance data and to cause display of information obtained from the logged performance data on the portable telecommunications device.

As a further example, the portable telecommunications device may be adapted to generate reference instructions or guidance for a user utilizing the logged performance data; the reference instructions or guidance comprising, for example, expected time to arrive at a target or check point, best course, speed up, down or maintain a constant speed for the physical wellbeing of a user.

In use, the portable telecommunications device may be activatable with different application software to utilize performance data collected by the performance monitoring module and data collected via the telecommunications network. For example, the portable telecommunications device may be adapted to collect data from a telecommunications network and to process the collected data with data collected by the performance monitoring module to produce information.

In addition or as an alternative to being a mere recipient of information, the portable telecommunications device may also be configured to be activatable to communicate the performance data or processed performance data to a telecommunications network. For example, the portable telecommunications device may be adapted to collect data from the performance monitoring module, and to transmit the collected data to a telecommunications network for processing at a remote station.

Such a capability is almost unknown in conventional bicycle computers or other mobile sports computers but is available through the present invention.

In an embodiment, the performance monitoring apparatus comprises a main casing, the main casing including mounting means for securing onto a user or a bicycle and a receptacle for securely receiving the performance monitoring module and the portable telecommunications device in mated connection.

The performance monitoring module may comprise a display for displaying performance data and a toggle switch, wherein the type of performance data to be instantaneously displayed is selectable by a user upon toggling of the toggle switch.

These and other features of the invention will be explained in further detail below.

BRIEF DESCRIPTION OF THE DRAWINGS

Exemplary embodiments of the present invention will be explained below by way of example and with reference to the accompanying drawings, in which.

DETAILED DESCRIPTION OF EXEMPLARY EMBODIMENTS

Figure 1:
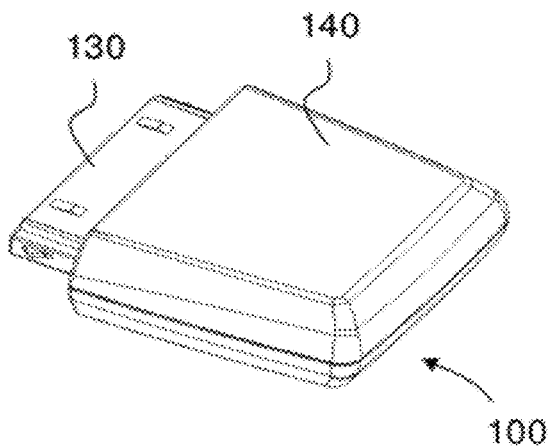
FIGS. 1 & 1A respectively depict perspective views from above and below of a bicycle computer module according to an embodiment of the present invention, FIGS. 2 & 2A respectively depict perspective views from above and below of the bicycle computer module of FIGS. 1 and 1A with the external housing removed.
Figure 1A:
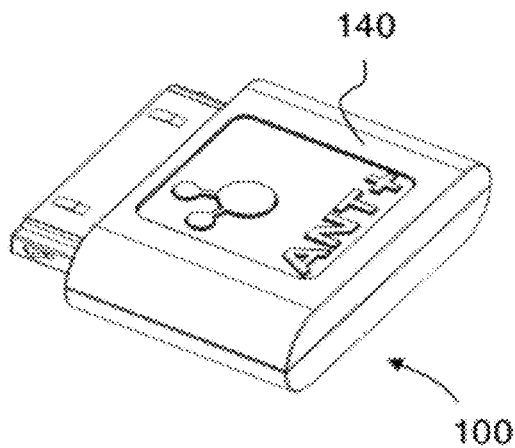

A bicycle computer module (nicked named 'bicycle computer dongle') 100 of FIGS. 1 to 5 as an example of a performance monitoring module of the present invention comprises a signal receiver 110, a micro-processor 120 and an adapter 130 which are housed within a rigid and moulded plastic housing 140. The signal receiver 110 comprises an antenna 112 for receiving radio frequency (RF) signals and an RF receiver 114 for frontend processing of RF signals received by the antenna and forwarding to the microprocessor 120.

The signal receiver is adapted to receive bicycle performance signals from bicycle performance sensors operating at 2.4 GHz using ANT® or ANT+® protocols and the received bicycle performance signals are processed by the microprocessor for output as bicycle performance data. The dongle is adapted to process common performance data such as speed, cadence and power, and the sensors therefore include respectively speed, cadence and power sensors.

The micro-processor 120 is a low-end 4 bit or 8-bit microprocessor which is pre-programmed to process bicycle performance signals received by the RF receiver and convert the received signals into performance data according to established methodology. The signal processing algorithms are pre-stored in the memory of the microprocessor, which also includes additional memory space for saving and logging performance data.

The adapter 130 is formed as a protrusion extending from the front end of the dongle, and is adapted for mating connection with a smart phone for applications to be described below. In addition, locking means are provided on the adapter to secure latching of the dongle onto a smart phone.

The dongle is of about bite size, measuring less than 5 cm long, 5 cm wide and 1 cm high, and weighs less than 80 gram. Because of such compactness and lightness, the dongle could be readily stored in a pocket of a user.

Figure 2:
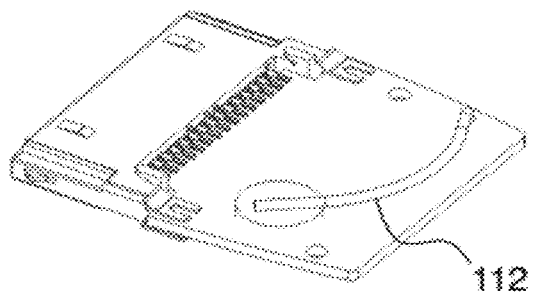
FIGS. 2B & 2C depict a top perspective view of a bicycle computer module according respectively to a second and a third embodiment of the present invention.
Figure 2A:
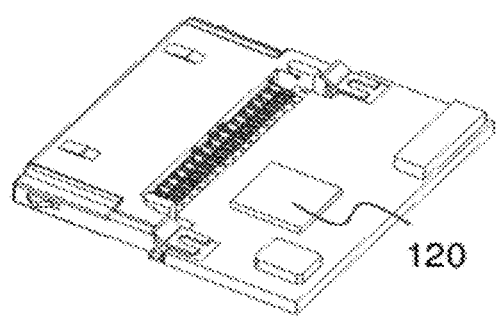
Figure 2B:
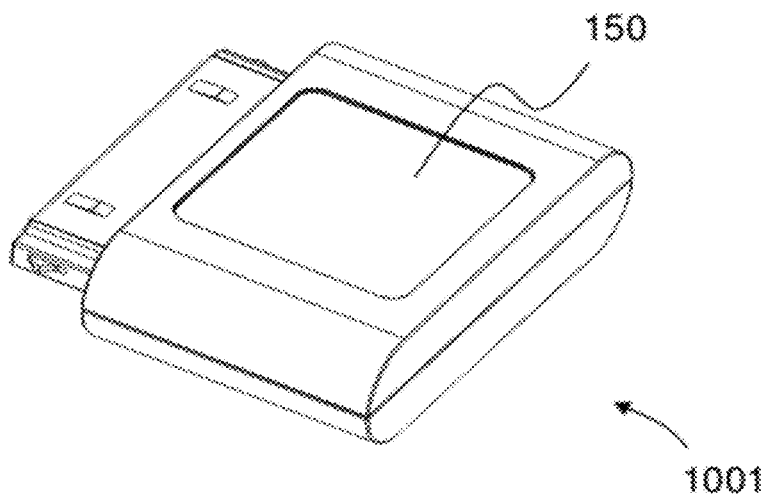

The dongle 1001 of FIG. 2B is substantially identical to that of FIG. 1, except that a window comprising a display screen 150 is provided for displaying performance and other data, such as operation conditions, battery level, RF signal reception level, or other operation indicators for reference by a user.

Figure 2C:
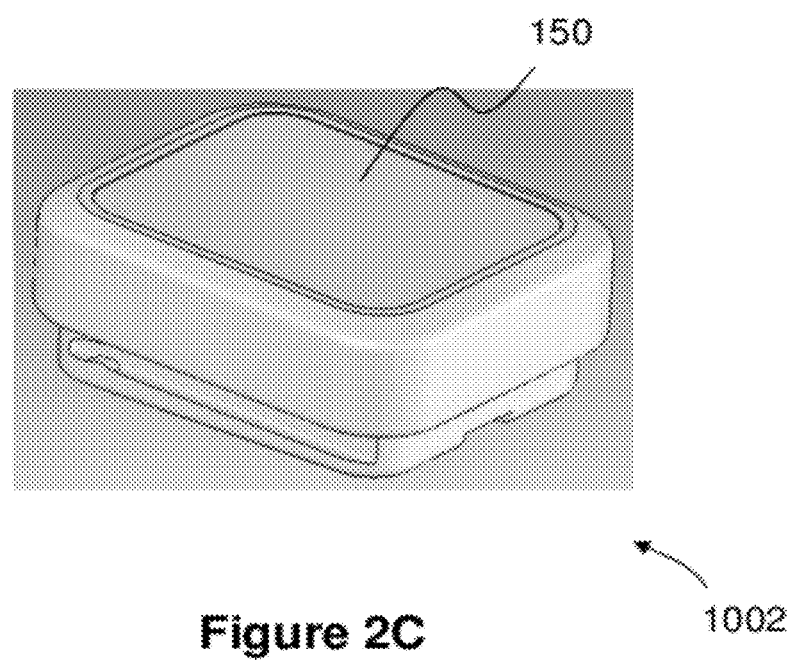
Figure 3:
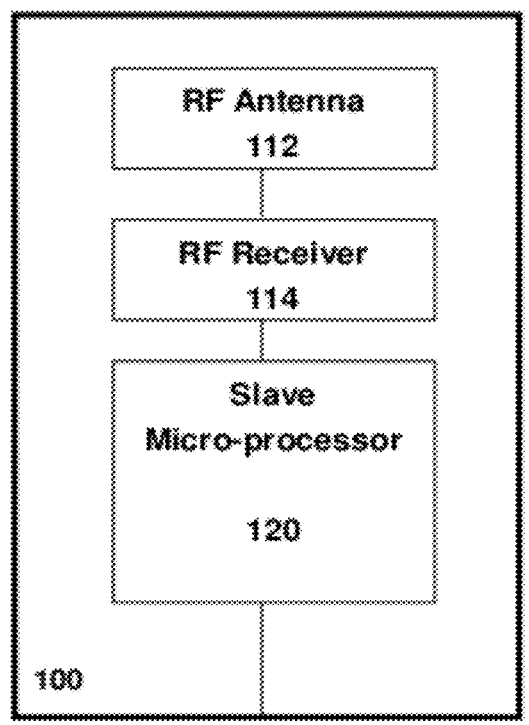
FIG. 3 is basic schematic circuit block diagram of the bicycle computer dongle of FIGS. 1 & 2.

The circuit arrangement of the dongle 1002 of FIG. 2C is substantively identical to that of FIG. 2B, except that the housing is modified for slide inserting into a mounting frame and a toggle switch protrudes from the bottom of the housing such that the information being displayed on the display screen could be selected by a user through switch toggling.

As components of the embodiments 100, 1001 and 1002 are substantially identical, the descriptions above on various parts of the dongle 100 are incorporated by reference into the dongles 1001 and 1002 and the same numerals will be used where appropriate.

Figure 4:
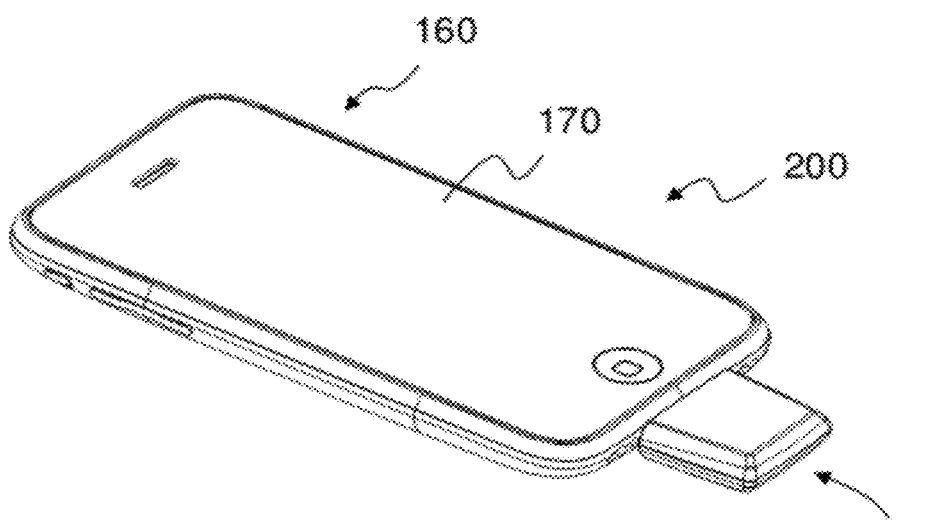
FIG. 4 is a perspective view depicting an exemplary embodiment of a bicycle computer apparatus of the present invention comprising the bicycle computer module of FIGS. 1 and 2 assembled with a smart mobile phone.

FIG. 4 depicts a bicycle computer 200 comprising an assembly of the dongle 100 and a smart mobile phone 160 in mating connection as an example of a bicycle computer apparatus of the present invention. The smart phone comprises a display screen 170, such as an LCD touch screen mounted on a plastic moulded housing, and other components of a typical smart phone such as an i-pod® or an i-phone® of Apple, Inc. The smart phone is installable with software such as application programs and operable by touching on the touch screen, features which are common in most available smart phones. The smart phone is provided with an input/output (I/O) port which is mechanically compatible with the adapter such that the dongle is detachably attachable to the smart phone.

Figure 5:
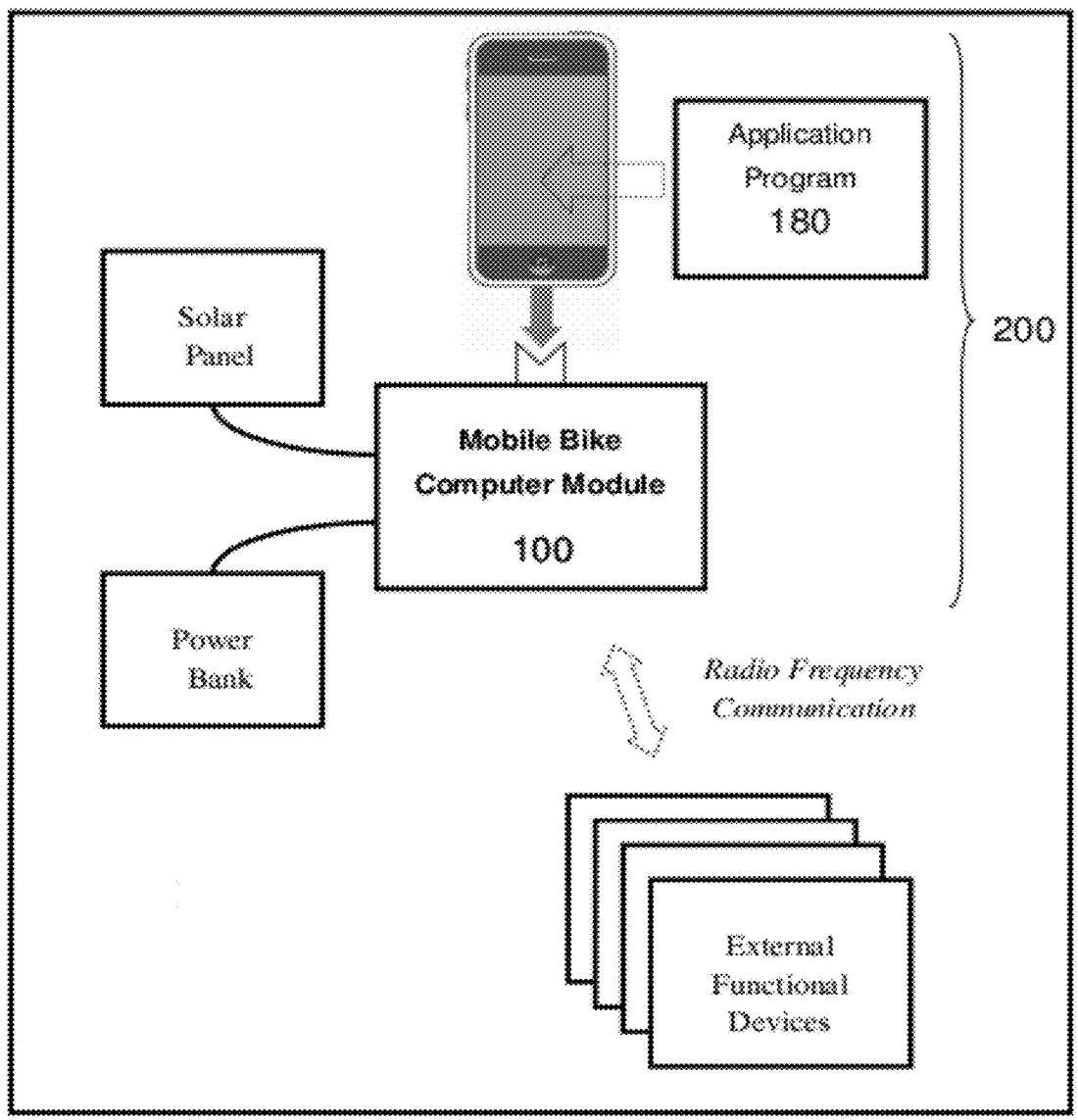
FIG. 5 is a schematic block diagram depicting exemplary functional blocks of the bicycle computer apparatus of FIG. 4.
Figure 6:
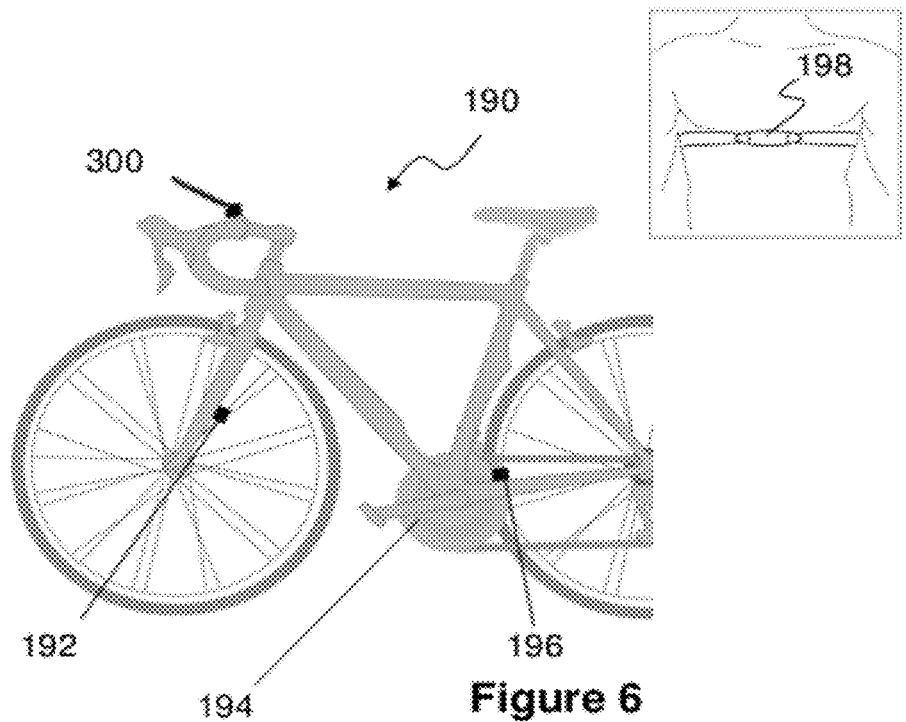
FIG. 6 depicts an exemplary use of the bicycle computer apparatus of FIG. 4 mounted as a bicycle computer pack on a bicycle.
Figure 7:
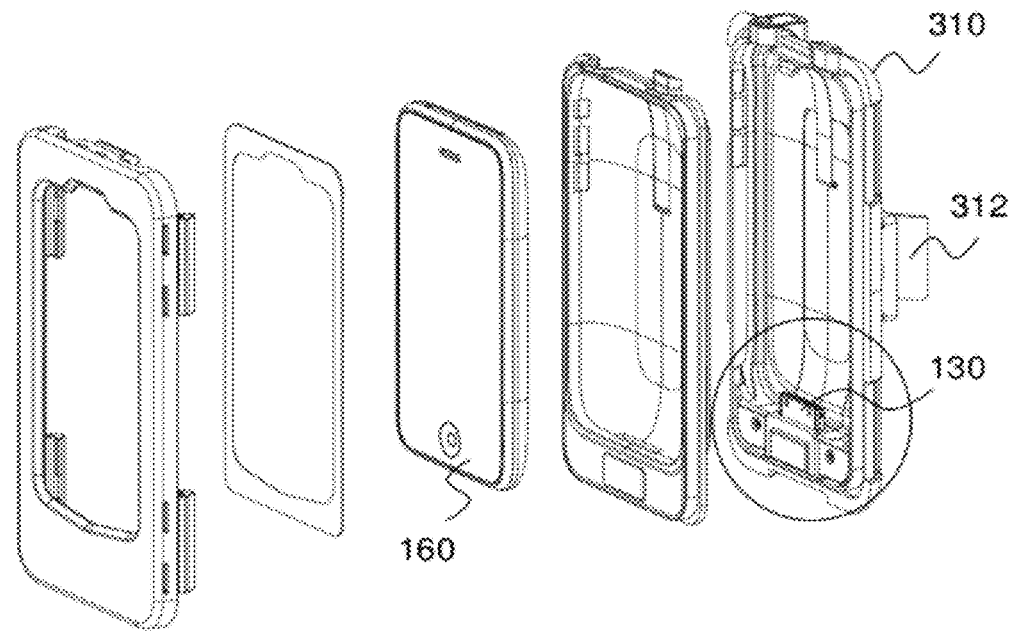
FIG. 7 shows an exploded view of the bicycle computer pack of FIG. 6.
Figure 7A:
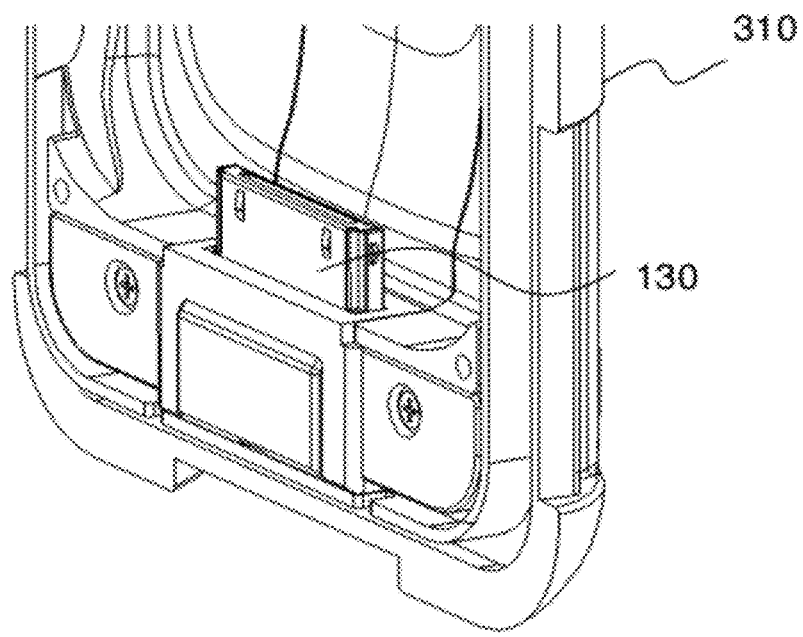
FIG. 7A is an enlarged view of the circled portion of FIG. 7.

Referring to FIG. 5, the smart phone is installed with application programs 180 for processing performance data collected by the dongle 100, and the dongle is operatively communicable with bicycle performance sensors or other external functional devices, such as solar panels or a power bank for powering the smart phone and/or the dongle, or physiological sensors such as ECG sensors, heart rate sensors, or blood sugar sensors. As shown in FIGS. 5&6, the physiological sensors are operatively connected to the dongle by a wireless link for convenience.

In use, the bicycle computer 200 is mounted as a single bicycle computer pack 300 on the front handle bar of a bicycle, as shown in FIG. 6. To detect performance parameters, a speed sensor 192, a power sensor 194, and a cadence sensor 196, a heart-rate sensor 198 are mounted on the bicycle and in wireless communication with the dongle installed on the bicycle computer pack. The bicycle computer pack 300 includes a bicycle computer 200 and a casing 310 including a receptacle for receiving the bicycle computer 200. The casing 310 comprises a hinged compartment defining the receptacle and includes a bicycle mount 312 for securing onto the bicycle frame. The inclination of the bicycle mount is adjustable to fit the personal preference of a rider for a comfortable view of information being displayed on the screen 170. When a rider has to leave the bicycle unattended, the rider may detach the pack 300 from the bicycle frame, or only removes the more valuable smart phone and dongle while leaving the casing attached to the bicycle.

Figure 9:
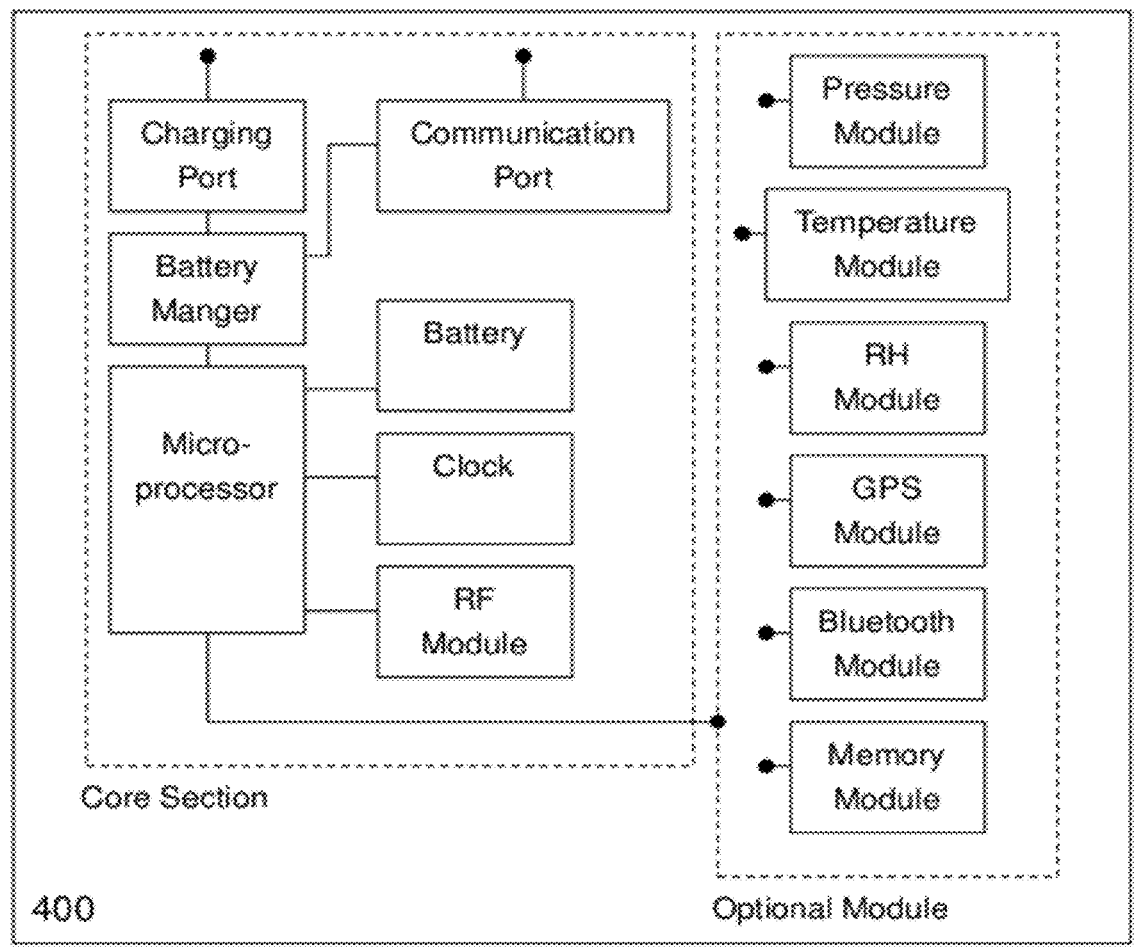
FIG. 9 shows a fourth embodiment of a bicycle computer module according to the present invention.

Because of the large processing power and memory of the smart phone, the bicycle computer is now configurable to process more varieties of signals, even though it has a relatively low-end processor and small memory. To capitalize on the versatility of this bicycle computer arrangement of the present invention, a bicycle computer dongle 400 with more complicated functionality as depicted in the block diagram of FIG. 9 is provided.

This bicycle computer dongle 400 is built on a relatively low-end and low-speed processor having a small built-in memory, but is programmed to cooperate with many varieties of sensors to meet the requirements of the more sophisticated users. More particularly, the dongle 400 is pre-arranged to operate with a combination of sensors for detecting environment parameters such as pressure, humidity, temperature, altitude, path or route, and/or distance-to-target; or physiological parameters such as blood pressure, blood oxygen, and/or body temperature.

Figure 8:
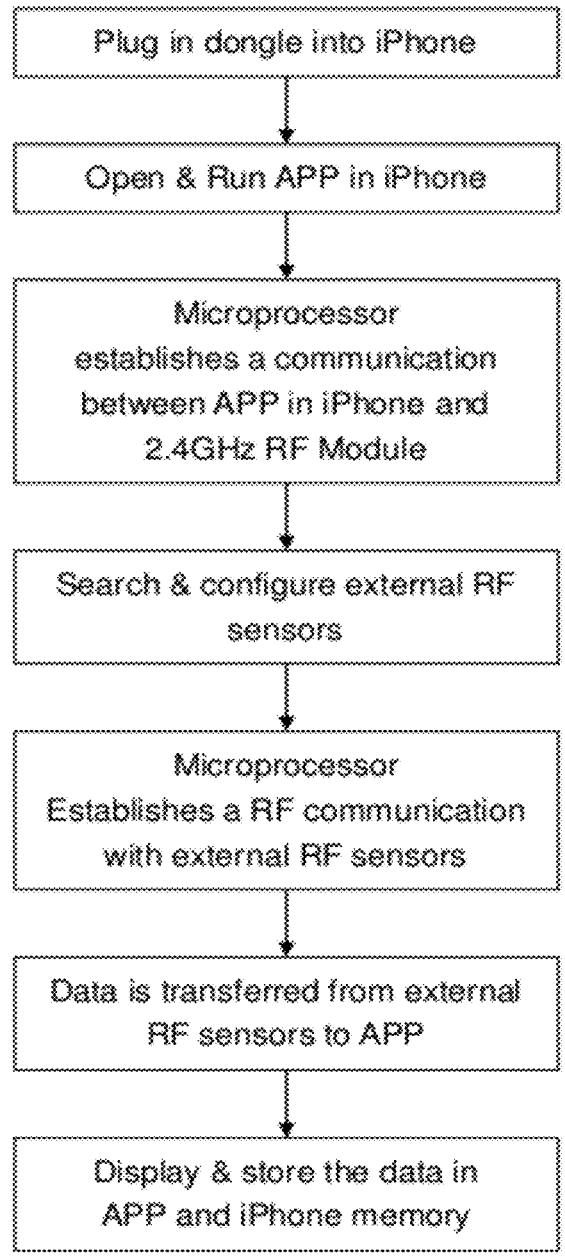
FIG. 8 is a flowchart depicting an exemplary operation flow of the bicycle computer apparatus of the present invention.

To operate the bicycle computer, a user will firstly plug the dongle 100 into the smart phone 160 to establish a communication link and turn on both devices, as illustrated in FIG. 8. After the initial starting up, the application software will operate and cause the microprocessor of the smart phone to establish a communication link between the smart phone and the RF receiver of the dongle. Next, the microprocessor of the smart phone will search for available sensors via the RF receiver. After the external sensors have been identified, the microprocessor will maintain an RF communication link with the sensors and to receive performance data from the sensors via the dongle. The dongle 100 provides initial performance signal to performance data conversion for onward transmission to the smart phone. Through configuration of the smart phone to cooperate with the specific features of the dongle by utilizing the fast processor and huge memory size of the smart, the bicycle computer 200 has a capability to handle and process signals from multiple sensors, and such a capability is unmatched by other known bicycle computers.

In operation, the microprocessor 120 of the dongle is operated to receive signals detected by the various sensors and to convert the received signals as performance data. In this application, the microprocessor 120 operates as a slave processor in response to instructions of the processor of the smart mobile phone 160. In the course of operation, the collected performance data are transmitted to the smart mobile phone for logging and further processing. Such a bicycle computer arrangement reduces the processing loading on the microprocessor 160 as well as the memory requirements of the dongle 100.

In a first mode of operation, performance data, such as speed, cadence, and/or distance travelled; and/or physiological data are displayed on the screen, and the information being displayed could be changed or selected by a user through tough screen operation.

In a second mode of operation, data collected by the dongle, whether environmental, physiological or otherwise, are processed by the smart phone together or in combination with other data collected by the smart phone to produce useful information. In a first example, the application software is configured to process GPS data collected by the smart phone via the telecommunications network to provide information, such as information on the course or the best course, available courses, expected time to arrive at a target, or expected distance to target; and to display the relevant information on the smart phone screen. In a second example, collected physiological data are processed by the smart phone to provide health information or advice to the rider. For example, the application program may be devised to monitor the body temperature, heart-rate or blood pressure of a rider and advise the rider to vary the speed or cadence in order to keep the body temperature, heart-rate or blood pressure below an acceptable or pre-determined level. In a third example, environmental data collected by the dongle are utilized by the smart phone to provide rider with information relating to anticipated performance of a rider. For example, the application program may be configured to correlate ambient temperature data and/or humidity and/or atmospheric pressure with heart-rate, blood pressure and/or body temperature etc to advise on a cycling pattern, such as the next rest session. In a fourth example, dongle collected data and smart phone collected date are selective used to devise a riding schedule. For example, to adjust a course or to change the speed to avoid lightning, thunderstorm or bad weather; or to select a course to meet a physical training program selected by a user, or to devise a preferred schedule or choice of schedules to avoid overloading a rider.

In a third mode of operation, the application software may be configured to transmit riding information obtained from data collected by the dongle, or data collected by both the dongle and the smart phone, to a remote station via a telecommunications network. The riding information may include, for example, location, rider fitness state, rider behavior, or rider tracking to facilitate remote tracking.

In a fourth mode of operation, the data transmitted to an external remote station may be further processed, and the processed information, which may contain instructions or guidelines, may be transmitted back to the bicycle computer via a telecommunications network.

While the invention has been explained with reference to the above exemplary embodiments, it would be appreciated to persons skilled in the art that the embodiments are only for illustration only and does not intend to limit on the scope of the invention. For example, while four exemplary modes of operation have been described above, many more modes are possible and the use of data or combination of data is without limit. Although the dongle and the sensors are described as linked by 2.4 GHz wireless channel, it would be appreciated that while the selected exemplary frequency channel is good for the purpose, other frequencies could be used and even wire connection could be used between the sensors and the dongle without loss of generality. Also, while the ANT® or ANT+® protocols are mentioned, other protocols could be used when desirable. Furthermore, while a smart phone such as i-pod or an i-phone has been used as an example of a suitable portable telecommunications device, mobile phones such as mobile phones for 2G, 3G or 4G systems are also suitable. In addition, while the dongle and the smart phone in the above exampled are connected in a mechanical mating manner, the dongle and the smart phone need not be mechanically attached and could be connected by wireless protocols such as Bluetooth®. In addition, while dongle 100 has been used to illustrate the embodiments of FIGS. 4-7A, it will be appreciated that the dongles 1001 and 1002 and other modifications could be used. Furthermore while smart phones with a touch screen provides a useful choice, mobile phones with control keypads or other control means such as a toggle switch are equally useful for cooperation with the dongles. While the communication interface of the exemplary dongle is adapted for wired data communication with the mobile phone, it will be appreciated that the data communication could be wireless.

Figure 10:
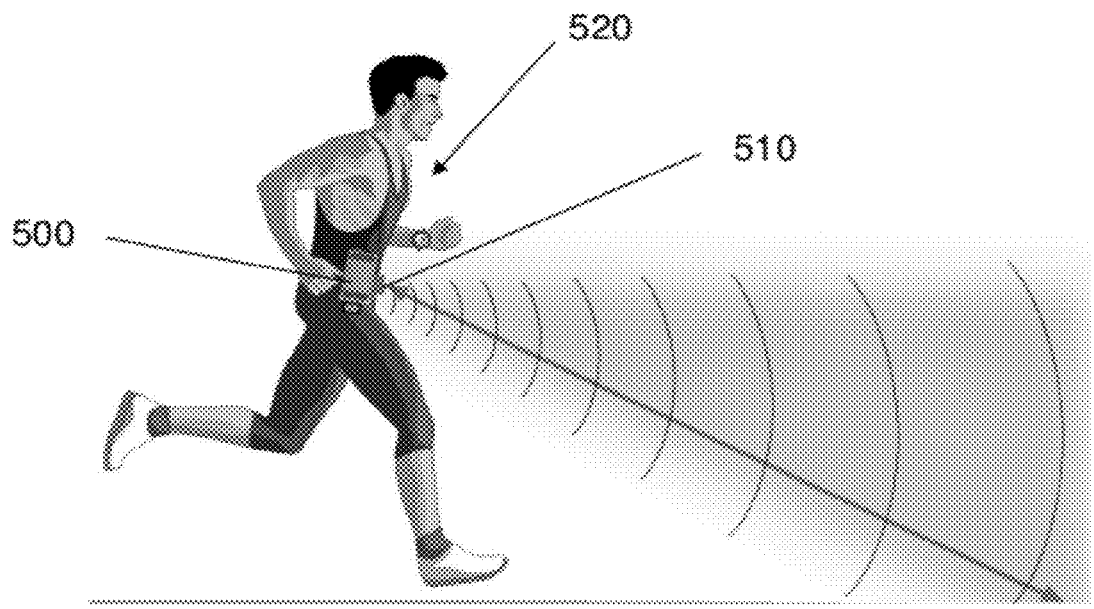
FIG. 10 depicts another embodiment of a sports performance monitor in another exemplary application.
Figure 11:
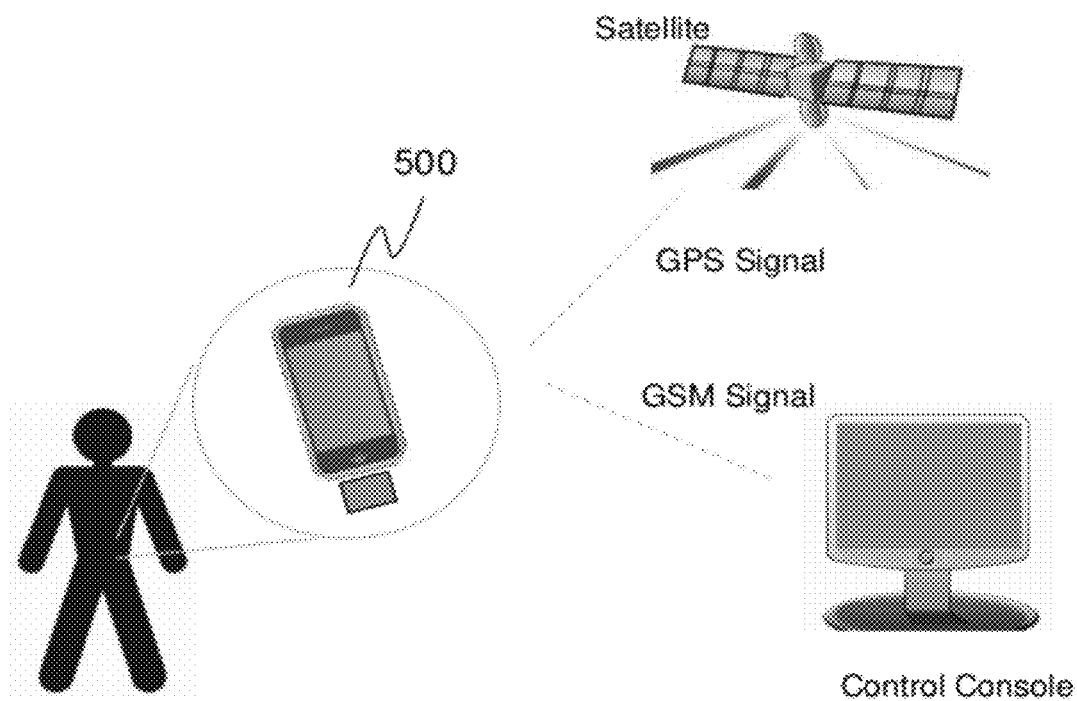
FIG. 11 is a schematic diagram illustrating an exemplary network application of the sports performance monitor of FIG. 10.

FIGS. 10 and 11 illustrate a runner's computer illustrating a second aspect of the present invention of a performance monitor. The runner's computer 500 comprises a smart phone and a runner's computer dongle. The runner's computer is substantially identical to that of the bicycle computer dongle 100 except that the microprocessor is adapted for monitoring running, such as step span, step frequency, step cadence, speed, and/or etc and the sensors are appropriated selected for that purposes. Similar to the bicycle computer, processing and telecommunications power of the smart phone is tapped to facilitate a more powerful running computer based on a dongle comprising a low-end cheap microprocessor to facilitate GPS, satellite, 2G to 4G, GSM or CDMA communications capability without loss of generality.

| Table of Numerals | |
|---|---|
| 100 | Bicycle computer dongle |
| 110 | Signal receiver |
| 112 | Antenna |
| 114 | RF receiver |
| 120 | Micro-processor |
| 130 | Adaptor |
| 140 | Housing |
| 150 | Display screen |
| 160 | Mobile phone |
| 170 | Display screen |
| 180 | Application program |
| 190 | Bicycle |
| 192 | Speed sensor |
| 194 | Power sensor |
| 196 | Cadence sensor |
| 198 | Heart-rate sensor |
| 200 | Bicycle computer |
| 300 | Pack |
| 310 | Casing |
| 312 | Bicycle mount |
| 400 | Bicycle computer dongle |
| 500 | Runner's computer |
| 1001 | Dongle |
| 1002 | Dongle |

The invention claimed is:

1. A performance monitoring apparatus comprising:
a performance monitoring module and a general purpose portable telecommunications device including at least one of a netbook computer, a mobile telephone, a smart mobile phone, and a super phone,
wherein the portable performance monitoring module comprises:
a signal receiver arranged to collect performance signals from at least one performance sensor;
a processor adapted for processing the collected performance signals to generate performance data, and for outputting the performance data to a general purpose portable telecommunications device; and
a communication interface for facilitating data communication with the portable telecommunications device,
and wherein:
the performance monitoring module or the processor of the performance monitoring module is arranged to communicate with the portable telecommunications device via the communication interface upon receipt of request from the portable telecommunications device,
the processor is configured as a slave processor to respond to control instructions of the portable telecommunications device, and
the portable telecommunications device is configured to collect geographic, weather or other data from a telecommunications network or other sources and generate reference instructions or guidance information for a user by utilizing at least one of performance data and environmental data collected by the performance monitoring module while the performance monitoring module is operating to receive performance signals from said performance sensor.

2. A performance monitoring apparatus according to claim 1, wherein
the portable telecommunications device is user activateable to capture, log, save and/or process for display performance data collected by the performance monitoring module upon execution of application software stored in said portable telecommunications device while the performance monitoring module is operating to receive performance signals from said performance sensor, and
the portable telecommunications device is arranged to process performance data collected by the performance monitoring module and/or data collected by the portable telecommunications device from a telecommunications network or other sources to generate information for use by a user upon execution of application software stored in said portable telecommunications device while the performance monitoring module is operating to receive said performance signals from said performance sensor.

3. A performance monitoring apparatus according to claim 2, wherein
the information generated by the portable telecommunications device includes at least one of information on available courses, the best course, expected time to arrive at target and expected distance to target,
the data collected by the portable telecommunications device from a telecommunications network include (i) geographical guidance data including at least one of GPS data, road, path, slope or landscape conditions or data, map data, altitude data, distance-to-target data, and amenities or (ii) weather data including at least one of atmospheric pressure, cloud, rain, and sunshine data, and
the portable telecommunications device is configured to selectively use data collected by at least one of the performance monitoring module and the portable telecommunications device to perform at least one of devising a riding schedule, adjusting a riding course, adjusting a course, and changing the speed while the performance monitoring module is operating to receive said performance signals from said performance sensor.

4. A performance monitoring apparatus according to claim 1, wherein
the portable telecommunications device is adapted to log and save both the performance data collected by the performance monitoring module and data collected from the telecommunications network, and
the portable telecommunications device is configured to process and/or analyze logged performance data and to cause display of information obtained from the logged performance data on the portable telecommunications device while the performance monitoring module is in operating to receive said performance signals from said performance sensor.

5. A performance monitoring apparatus according to claim 1, wherein the portable telecommunications device is adapted to generate reference instructions or guidance for a user utilizing logged performance data while the performance module is operating to receive performance signals, said reference instructions or guidance including at least one of (i) expected time to arrive at a target or check point, (ii) best course, and (iii) speed up, down or maintain a constant speed for the physical wellbeing of a user.

6. A performance monitoring apparatus according to claim 1, wherein the portable telecommunications device is activatable with different application software to utilize performance data collected by the performance monitoring module and data collected via the telecommunications network while the performance monitoring module is operating to receive said performance signals from said performance sensor.

7. A performance monitoring apparatus according to claim 6, wherein the portable telecommunications device is also activatable to communicate the performance data or processed performance data to a telecommunications network while the performance monitoring module is operating to receive said performance signals from said performance sensor.

8. A performance monitoring apparatus according to claim 1, wherein
the performance monitoring module and the general purpose portable telecommunications device are detachable by a mechanical mating connection means, and
the apparatus comprises a main casing, the main casing including mounting means for securing onto a user or a bicycle and a receptacle for securely receiving the performance monitoring module and the portable telecommunications device in mated connection.

9. A performance monitoring apparatus according to claim 8, further comprising a display for displaying performance data and a toggle switch, wherein the type of performance data to be instantaneously displayed is selectable by a user upon toggling of the toggle switch while the performance monitoring module is operating to receive said performance signals from said performance sensor.

10. A performance monitoring apparatus according to claim 9, wherein the portable telecommunications device is adapted to collect data from the performance monitoring module, and to transmit the collected data to a telecommunications network for processing at a remote station while the performance monitoring module is operating to receive said performance signals from said performance sensor.

11. A performance monitoring apparatus according to claim 10, wherein the portable telecommunications device is adapted to collect data from a telecommunications network and to process the collected data with data collected by the performance monitoring module to produce information for user reference while the performance monitoring module is operating to receive said performance signals from said performance sensor.

12. A performance monitoring apparatus according to claim 8, wherein the performance monitoring module is a bicycle computer module.

13. A performance monitoring apparatus comprising:
a performance monitoring module and a general purpose portable telecommunications device including at least one of a netbook computer, a mobile telephone, a smart mobile phone, and a super phone,
wherein the portable performance monitoring module comprises:
a signal receiver arranged to collect performance signals from at least one performance sensor;
a processor adapted for processing the collected performance signals to generate performance data, and for outputting the performance data to a general purpose portable telecommunications device; and
a communication interface for facilitating data communication with the portable telecommunications device,
and wherein:
the performance monitoring module or the processor of the performance monitoring module is arranged to communicate with the portable telecommunications device via the communication interface upon receipt of request from the portable telecommunications device,
the processor is configured as a slave processor to respond to control instructions of the portable telecommunications device, and
the portable telecommunications device is configured to search for available performance sensors via the performance monitoring module and to receive performance data from the performance sensors via the performance monitoring module while operating to receive performance signals.

14. A performance monitoring apparatus according to claim 13, wherein
the portable telecommunications device is user activateable to capture, log, save and/or process for display performance data collected by the performance monitoring module upon execution of application software stored in said portable telecommunications device while the performance monitoring module is operating to receive performance signals from said performance sensor.

15. A performance monitoring apparatus according to claim 14, wherein
the information generated by the portable telecommunications device includes at least one of information on available courses, the best course, expected time to arrive at target and expected distance to target,
the data collected by the portable telecommunications device from a telecommunications network include (i) geographical guidance data including at least one of GPS data, road, path, slope or landscape conditions or data, map data, altitude data, distance-to-target data, and amenities or (ii) weather data including at least one of atmospheric pressure, cloud, rain, and sunshine data, and
the portable telecommunications device is configured to selectively use data collected by at least one of the performance monitoring module and the portable telecommunications device to perform at least one of devising a riding schedule, adjusting a riding course, adjusting a course, and changing the speed while the performance monitoring module is operating to receive said performance signals from said performance sensor.

16. A performance monitoring apparatus according to claim 13, wherein
the portable telecommunications device is arranged to process performance data collected by the performance monitoring module and/or data collected by the portable telecommunications device from a telecommunications network or other sources to generate information for use by a user upon execution of application software stored in said portable telecommunications device while the performance monitoring module is operating to receive said performance signals from said performance sensor.

17. A performance monitoring apparatus according to claim 13, wherein
the portable telecommunications device is adapted to log and save both the performance data collected by the performance monitoring module and data collected from the telecommunications network, and
the portable telecommunications device is configured to process and/or analyze logged performance data and to cause display of information obtained from the logged performance data on the portable telecommunications device while the performance monitoring module is in operating to receive said performance signals from said performance sensor.

18. A performance monitoring apparatus according to claim 13, wherein the portable telecommunications device is adapted to generate reference instructions or guidance for a user utilizing logged performance data while the performance module is operating to receive performance signals, said reference instructions or guidance including at least one of (i) expected time to arrive at a target or check point, (ii) best course, and (iii) speed up, down or maintain a constant speed for the physical wellbeing of a user.

19. A performance monitoring apparatus according to claim 13, wherein the portable telecommunications device is activatable with different application software to utilize performance data collected by the performance monitoring module and data collected via the telecommunications network while the performance monitoring module is operating to receive said performance signals from said performance sensor.

20. A performance monitoring apparatus according to claim 19, wherein the portable telecommunications device is also activatable to communicate the performance data or processed performance data to a telecommunications network while the performance monitoring module is operating to receive said performance signals from said performance sensor.

21. A performance monitoring apparatus according to claim 13, wherein
the performance monitoring module and the general purpose portable telecommunications device are detachable by a mechanical mating connection means, and
the apparatus comprises a main casing, the main casing including mounting means for securing onto a user or a bicycle and a receptacle for securely receiving the performance monitoring module and the portable telecommunications device in mated connection.

* * * * *